(12) United States Patent
Pollack et al.

(10) Patent No.: US 10,145,857 B2
(45) Date of Patent: Dec. 4, 2018

(54) TUBE TRAY VISION SYSTEM

(71) Applicant: Siemens Healthcare Diagnostics Inc., Tarrytown, NY (US)

(72) Inventors: Benjamin Pollack, Budd Lake, NJ (US); Ryan German, Riverdale, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 256 days.

(21) Appl. No.: 14/774,794

(22) PCT Filed: Mar. 14, 2014

(86) PCT No.: PCT/US2014/027217
§ 371 (c)(1),
(2) Date: Sep. 11, 2015

(87) PCT Pub. No.: WO2014/152329
PCT Pub. Date: Sep. 25, 2014

(65) Prior Publication Data
US 2016/0025757 A1    Jan. 28, 2016

Related U.S. Application Data

(60) Provisional application No. 61/782,435, filed on Mar. 14, 2013.

(51) Int. Cl.
*G01N 35/02* (2006.01)
*G01N 35/00* (2006.01)
(Continued)

(52) U.S. Cl.
CPC .............. *G01N 35/02* (2013.01); *G01D 5/32* (2013.01); *G01N 21/253* (2013.01); *G01N 35/00* (2013.01);
(Continued)

(58) Field of Classification Search
CPC ....... G01N 21/253; G01N 35/00; G01N 35/02
See application file for complete search history.

(56) References Cited

U.S. PATENT DOCUMENTS

| | | | |
|---|---|---|---|
| 4,931,402 | A | 6/1990 | Abplanalp |
| 6,136,274 | A | 10/2000 | Nova et al. |

(Continued)

OTHER PUBLICATIONS

PCT International Search Report and Written Opinion dated Jul. 29, 2014 (7 Pages).

*Primary Examiner* — James M Pontius
*Assistant Examiner* — Kyle M Lotfi (57) ABSTRACT

Images of a tube tray, which fits within a drawer and holds tubes in slots arranged in rows and columns, are captured to determine characteristics related to the tube tray. By analyzing the images, features of the tubes are determined, providing valuable information in an IVD environment in which a sample handler is processing the tubes. Each row of the tube tray is encoded to allow for detection of a new row moving into focus of cameras. The cameras capture an image of the tube tray, and the image is stored in a memory buffer. When the next row moves into focus, a subsequent image is taken and stored. The result is a series of images providing multi-perspective views of the rows of the tube tray. The images are analyzed to determine characteristics of the tubes, which are utilized by the sample handler in processing the tubes.

22 Claims, 8 Drawing Sheets

(51) Int. Cl.
   *G01N 21/25*   (2006.01)
   *G01D 5/32*    (2006.01)
   *H04N 5/225*   (2006.01)
   *H04N 7/18*    (2006.01)
   *G01N 35/04*   (2006.01)

(52) U.S. Cl.
   CPC ........... *H04N 5/2256* (2013.01); *H04N 7/183* (2013.01); *G01N 2035/0418* (2013.01); *G01N 2035/0498* (2013.01)

(56) References Cited

U.S. PATENT DOCUMENTS

| | | | |
|---|---|---|---|
| 9,651,499 B2* | 5/2017 | Mahuna | G01N 21/8851 |
| 2005/0142033 A1 | 6/2005 | Glezer et al. | |
| 2010/0028124 A1 | 2/2010 | Lackner et al. | |
| 2011/0071039 A1 | 3/2011 | Kumar et al. | |
| 2014/0163920 A1* | 6/2014 | Jorgensen | B01L 3/545 |
| | | | 702/127 |
| 2014/0305227 A1* | 10/2014 | Johns | B01D 21/262 |
| | | | 73/863.01 |

* cited by examiner

TUBE TRAY VISION SYSTEM

CROSS REFERENCE TO RELATED APPLICATIONS

This application claims priority to U.S. provisional application Ser. No. 61/782,435, filed Mar. 14, 2013, which is incorporated herein by reference in its entirety.

TECHNOLOGY FIELD

The present invention relates generally to characterizing tubes contained in a tube tray and, more particularly, to capturing images of a tube tray to determine characteristics of the tubes held within the tray.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) into which tubes or vials containing patient samples have been loaded. Because of the variety of assays needed in a modern IVD lab, and the volume of testing necessary to operate a lab, multiple analyzers are often employed in a single lab. Between and amongst analyzers, automation systems may also be used. Samples may be transported from a doctor's office to a lab, stored in the lab, placed into an automation system or analyzer, and stored for subsequent testing.

Storage and transport between analyzers is typically done using trays. A tray is typically an array of several patient samples stored in test tubes. These trays are often stackable and facilitate easy carrying of multiple samples from one part of the laboratory to another. For example, a laboratory may receive a tray of patient samples for testing from a hospital or clinic. That tray of patient samples can be stored in refrigerators in the laboratory. Trays of patient samples can also be stored in drawers. In some automation systems, an analyzer can accept a tray of patient samples and handle the samples accordingly, while some analyzers may require that samples be removed from trays by the operator and placed into carriers (such as pucks) before further handling. Trays are generally passive devices that allow samples to be carried and, in some cases, arranged in an ordered relationship.

Generally, information about sample tubes stored in a tray is not known until an operator or sample handling mechanism interacts with each tube. For example, a sample handling robot arm may pick up a tube, remove it from the tray, and place it into a carrier. The carrier can then travel to a decapper station to remove any possible cap and pass by a barcode reader so that a barcode on the side of the tube can be read to reveal the contents of the tube. In many prior art sample handling mechanisms, the identity of the tube is not known until after the tube is removed from the tray. In this manner, all tubes in a tray will often be handled the same way until after a tube is placed onto a carrier in an automation system.

SUMMARY

It is desirable to ascertain various pieces of information relating to a tray, the tubes, and the tubes' location within the tray, such as, for example, the tray slots containing a tube; a tube's center point, diameter, and height; the tray's orientation within a drawer; whether a tube is covered with a cap or tube-top cup; a barcode on a top surface of a cap; and a speed at which a drawer holding the tray is being inserted or removed into the work environment. It is desirable to obtain these and other pieces of information quickly, without expensive equipment, and without handling or touching the tubes. Such knowledge allows for an efficient and streamlined processing of the tubes, as well as for reduced setup and maintenance costs.

Embodiments of the present invention address the above needs by providing a characterization of tube trays by capturing images of the trays.

Embodiments of the present invention provide a system and a method for characterizing a tube tray handled by a sample handler in an in vitro diagnostics (IVD) environment, the tube tray configured to fit within a portion of a drawer that is movable between an open and a closed position and that is accessible by the sample handler, the tube tray comprising an array of rows and columns of slots, each slot configured to hold a tube.

According to aspects of the present invention, an image capture system, comprised of at least one camera, is configured to capture images of the tube tray positioned in the drawer; an encoder in communication with the image capture system is configured to detect movement of the tube tray in the drawer; and one or more processors are together configured to receive images taken by the image capture system and analyze the images. The encoder transmits a signal to the image capture system upon detection of movement of the tube tray corresponding to a new row of the tube tray moving into a substantially centered position beneath the at least one camera of the image capture system (e.g., the row is substantially centered horizontally or vertically amongst the other rows in an image). The signal serves as an instruction for the image capture system to take an image of the new row. The one or more processors process a series of images of the new row to determine characteristics related to tubes held in slots of the new row.

According to an embodiment, the series of images of the new row comprise an image of the new row in the substantially centered position, as well as one or more images of adjacent rows of the new row in a substantially centered position beneath the at least one camera of the image capture system. The one or more images of adjacent rows provide a perspective view of the new row, wherein the one or more processors analyze the new row based upon the perspective view and the substantially centered position view of the new row.

According to an additional aspect, a drawer sensor is configured to detect one or more of (i) the drawer being fully closed and (ii) the drawer being fully opened. The drawer sensor signals to the one or more processors upon detection of the drawer being fully closed. The one or more processors begin the processing of the series of images of the new row upon receipt of the signal from the drawer sensor.

In some embodiments, the image capture system includes a lighting source.

According to an embodiment, the characteristics related to tubes held in slots of the new row are communicated to a module of the sample handler. The characteristics may include one or more of: a height of one or more tubes, a diameter of one or more tubes, a center point of one or more tubes, whether one or more tubes have a cap or tube-top cup, barcode information on a top surface of a cap on one or more tubes, a color of a cap on one or more tubes, a type of a cap or tube-top cup on one or more tubes, a type of tube, a type of sample, a priority of the tubes, an orientation of one or more tubes, and the tube tray slots containing a tube.

According to an embodiment, the characteristics related to tubes held in slots of the new row comprise one or more of: detecting the presence of condensation on at least one tube, detecting the presence of bubbles in at least one tube, detecting a fluid height of a fluid in at least one tube, detecting damage to at least one tube, detecting one or more anomalous quality of a sample contained in at least one tube, and detecting problems with a barcode on at least one tube.

According to an embodiment, one or more processors process a series of images of the new row to determine one or more characteristics of the tube tray, comprising at least one of: an identity of the tube tray, the presence of debris or spillage in a slot of the tube tray, an orientation of the tube tray, and damage to the tube tray.

According to an embodiment, the tube tray has visual markings between slots to identify the rows of the tube tray, wherein the one or more processors use the visual markings to confirm the new row in the series of images being processed.

In an embodiment, one or more memory buffer devices comprise look-up tables containing parameter and calibration data related to the tubes, the look-up tables accessible by the one or more processors for processing the series of the images.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention relate to capturing images of a tube tray configured to fit within a drawer and hold a plurality of tubes in slots that are arranged in an array of rows and columns. The images are used to characterize the tray as well as the tubes held on the tray. In particular, according to embodiments, by analyzing the images, various features of the tubes can be determined, such as, for example, the height, diameter, and center point of the tubes, whether the tubes have a cap or tube-top cup, the barcodes on top surfaces of the tubes (e.g., on a cap), and the tray slots containing a tube. Other features of sample tubes that may be determined via these images are discussed throughout. This information is valuable in an IVD environment in which a sample handler is processing the tubes and moving the tubes to analyzers for testing and analysis. Embodiments of the present invention are particularly well suited for, but in no way limited to, IVD environments.

Figure 1:
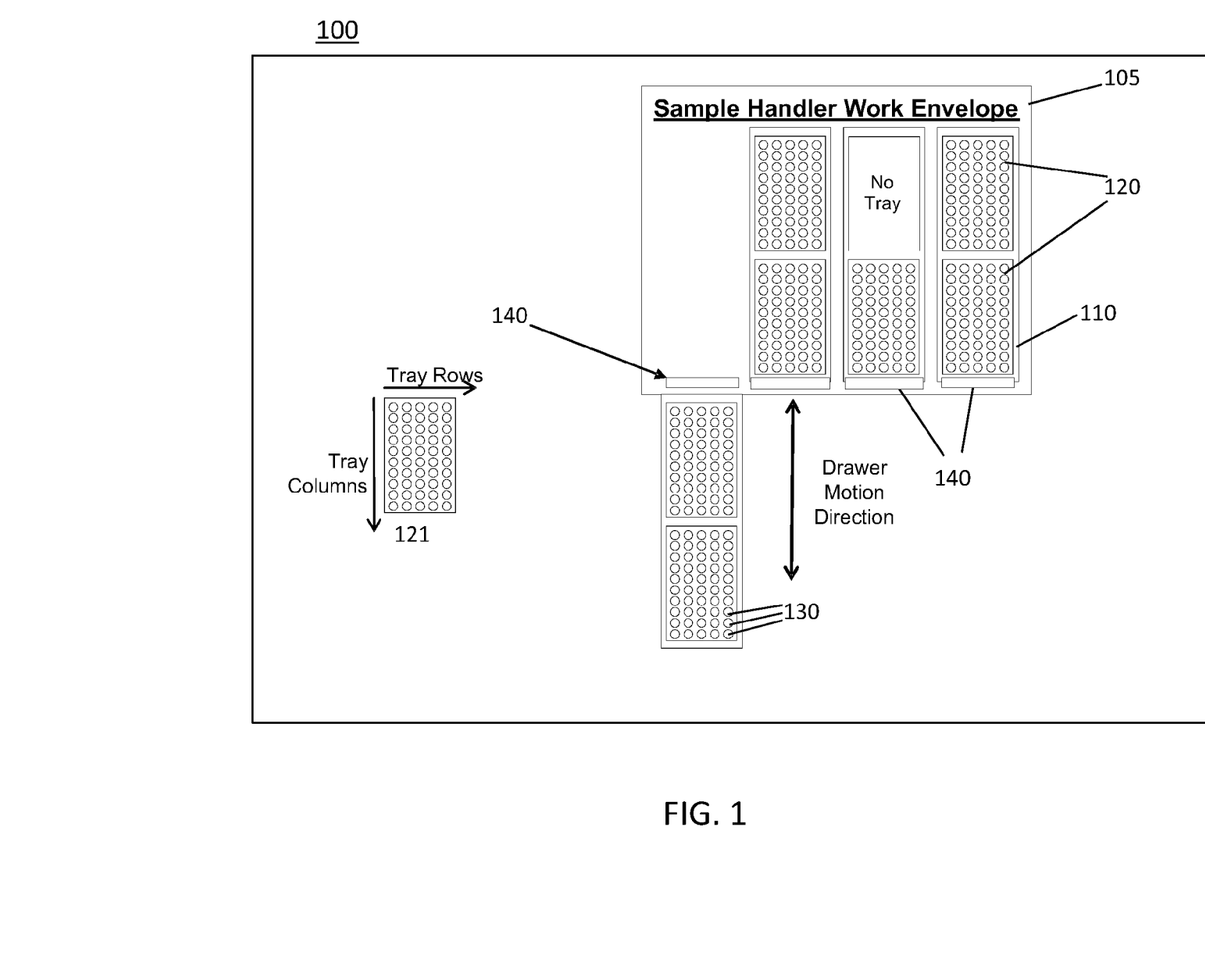
FIG. 1 is a representation of a system for characterizing through image analysis tube trays and tubes held in a drawer, according to an embodiment.

FIG. 1 is a representation of a system 100 in which tube trays 120 and tubes 130 contained thereon are characterized by obtaining and analyzing images thereof, according to an embodiment. One or more drawers 110 are movable between an open and a closed position and are provided in a work envelope 105 for a sample handler. One or more tube trays 120 may be loaded into a drawer 110 or may be a permanent feature of the drawer 110. Each tube tray 120 has an array of rows and columns of slots (as depicted in exemplary tray 121) in which tubes 130 may be held.

According to embodiments, images are taken of a tube tray 120; the images are analyzed to determine characteristics of the tube tray 120 and the tubes 130. A moving-tray/fixed camera approach is used, according to embodiments provided herein, to capture the images for analysis thereof. As the tube tray 120 is moved into the work envelope 105 by, for example, manually or automatically pushing in the drawer 110, an image capture system 140 is used to take images of the tube tray 120 and the tubes 130 contained thereon. According to an embodiment, the image capture system 140 includes one or more cameras positioned at or near the entrance to the work envelope 105. The one or more cameras may be positioned above the surface of the tube tray 120. For example, the cameras may be placed three to six inches above the surface to capture a high resolution image of the tube tray 120. Other distances and/or positioning may also be used depending on the features of the cameras and the desired perspective and image quality. Optionally, the image capture system 140 may include one or more lighting sources, such as an LED flash. As the tube tray 120 is already required to be slid into the work envelope 105, adding the fixed image capture system 140 does not add an excess of cost or complexity to the work envelope 105. The image capture system 140 also includes one or more processors to perform the image capture algorithms, as further described below.

According to an embodiment, the image capture system 140 captures an image each time a row of the tube tray 120 is moved into a center position or a position substantially centered under the one or more cameras. More than one row of the tubes 130 can be captured in this image, with one row being centered or substantially centered beneath the image capture system 140, while adjacent rows are captured from an oblique angle in the same image. By capturing more than one row at a time, the rows of tubes 130 are captured from multiple perspectives, providing for depth and perspective information to be captured in the images for each tube 130.

According to an embodiment, a tri-scopic perspective of a row of tubes 130 is captured as the row of tubes 130 are captured in multiple images. For example, a single row may appear in the bottom portion of an image (from an oblique perspective) when the preceding row is centered or substantially centered beneath the image capture system 140; that single row may then appear substantially centered in an image (from a substantially top-down perspective) when the row of tubes 130 itself is centered or substantially centered beneath the image capture system 140; and that single row may appear in the top portion of an image (from another oblique perspective) and when the subsequent row of tubes 130 is centered or substantially centered beneath the image capture system 140. In another embodiment, a stereoscopic perspective of a row of tubes 130 may be captured as images are taken when the image capture system 140 is centered or substantially centered above a point between two adjacent rows (allowing each row to appear in two images at two oblique perspectives). Similarly, rows may appear in more than three images, in more than three perspectives, allowing more three-dimensional information about each tube to be gleaned from a plurality of images. The invention is not limited to tri-scopic and stereoscopic perspectives of the row of tubes 130; instead, depending on features of the cameras and the positioning of the image capture system 140 with respect to the work envelope 105, additional perspectives may be obtained.

Figure 2A:
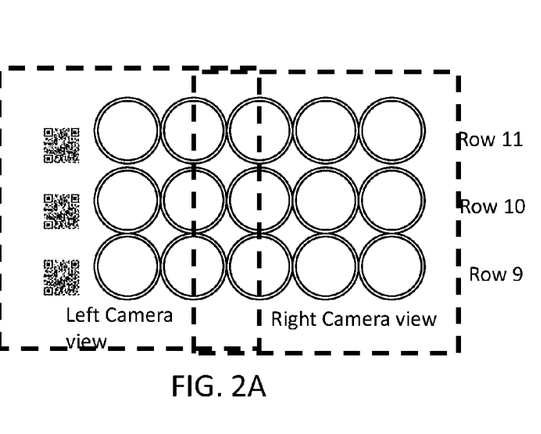
FIGS. 2A-2F provide illustrations of a work envelope as exemplary images are captured for a row of tubes, according to an embodiment.
Figure 2B:
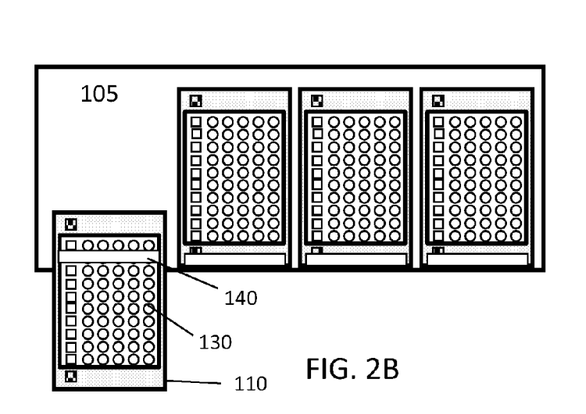
Figure 2C:
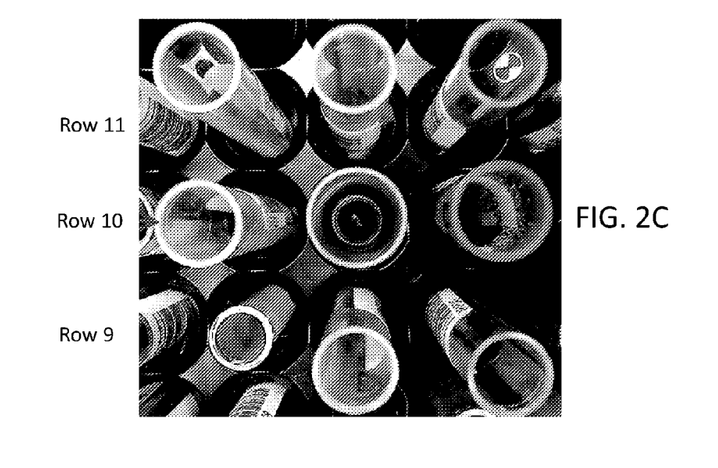
Figure 2D:
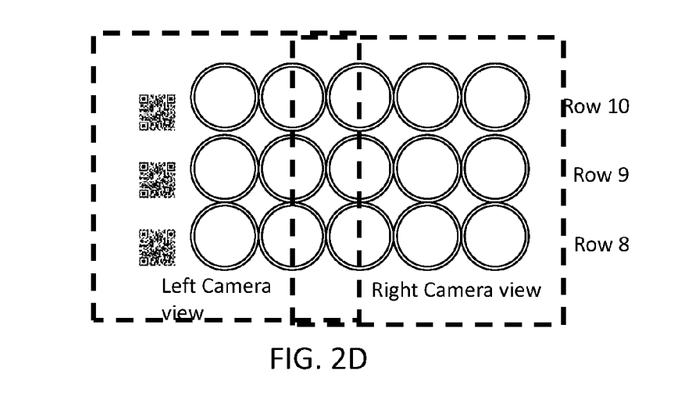
Figure 2E:
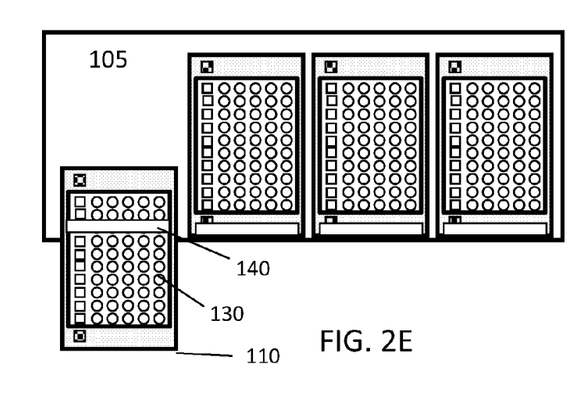
Figure 2F:
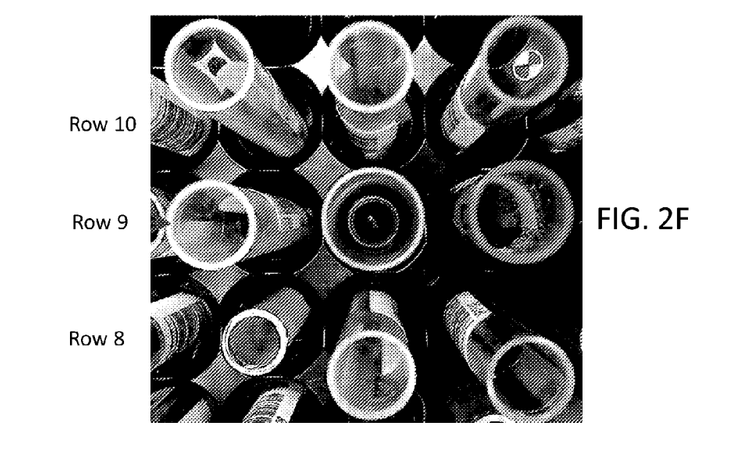

FIGS. 2A-2F provide illustrations of the work envelope 105 as exemplary images are captured for a row of tubes 130. The image capture system 140 captures multiple perspectives of the row of the tubes 130 as the row is advanced into the work envelope 105. As shown in FIGS. 2A-2C, an image of row 10 is captured directly or near directly under the one or more cameras as row 10 is moving into the work envelope 105 (i.e., the drawer 110 is being slid into the work envelope 105), allowing row 10 to appear substantially in the center of the image (e.g., as shown in FIG. 2C). In this example, two cameras are used, a right and a left camera. FIG. 2A illustrates the fields of view of these cameras at an image of row 10. In some embodiments, the fields of view of these cameras can overlap. FIG. 2B shows the exemplary situation that allows the images to be captured. As drawer 110 is closed, row 130 passes through the field of view of image capture system 140, allowing successive images to be taken. FIG. 2C shows an exemplary grayscale image that can be captured, showing an overhead image of row 10 and oblique images of rows 9 and 11. Similar images can be captured overhead rows 9 and 11 as the drawer 110 is closed. FIGS. 2D-2F illustrate the subsequent oblique perspective image (e.g., as shown in FIG. 2F) of row 10 (and overhead image of row 9, and oblique perspective image of row 8) that is captured as row 10 is advanced further into the work envelope 105 and as row 9 is centered or substantially centered beneath the one or more cameras. The series of FIGS. 2A-2F illustrate the depth of information that is obtained from the images, enabling the determination of the following characteristics: a center point of each tube in set 130 (e.g., the x-y location determined by correlating image features corresponding to a tube holder); a height of each tube (e.g., correlated to the pixel distance of the top of the tube between two adjacent images); a diameter of each tube (e.g., by observing the pixel size of the circle or oval formed at the top of each tube or by the pixel distance between each side of the tube in each image); if a tube 130 has a cap or tube-top cup on its top surface; identification information on a tube 130 (i.e., an identifier, such as a barcode, placed on a cap of a tube 130); or other characteristics that will be apparent to a person of ordinary skill.

In some embodiments, one or two dimensional barcodes/QR codes can be placed on tube caps or on the surface of a tray. The images captured via image capture system 140 can be processed to read this information. This can reveal the identity of a sample contained in a sample tube or information about the properties of the sample, such as the type of bodily fluid contained or whether the sample is high priority. In some embodiments, the color of the cap can indicate priority, type, or other status information, and can be determined by processing images captured by the image capture system. In some embodiments, the color or label observed by the image capture system can indicate that the sample tube contains a calibrating fluid or control.

In some embodiments, multiple types of trays can be used. For example, larger trays can be used to transport a greater number of sample tubes, while smaller trays may be used to transport a smaller number of samples, which may be useful when transporting specialized sample tubes, such as calibrators and STAT samples. The type of tray can be conveyed to the image capture system 140 via optical marks like QR codes on the tray. QR codes or other optical marks can also convey tray orientation, tray priority, identity/serial number, size, and physical properties (such as number of slots, version, etc.) to the image capture system. By analyzing images captured of the marks, a drawer vision system can quickly anticipate the extent of a tray and better analyze the images of tubes, in some embodiments, by using a model of the tray based on information received from the optical marks.

In some embodiments, when the sample tube lacks a cap, the images captured via image capture system 140 can be processed to determine information about the quality of the sample and any defects or anomalous characteristics of a sample tube or tray at an early stage in the process. For example, peeling labels on the side of a sample tube can cause problems with subsequent handling. A peeling label may be visible in the top-down or oblique images if it does not lay flat on the tube surface. If a tube is wet or has condensation, it may cause problems with gripping. Condensation droplets may be observable as refractive or reflective beads if severe enough. If a tube has a crack or other physical defect, this can be observable and detected during image analysis of the top-down or oblique images. Image analysis can also detect that a tube is tilted relative to other tubes, which may be useful in positioning the sample handling robot arm when it interacts with the tube.

If a sample has been mishandled, it can froth or bubble. This may affect readings later and can be detected via image analysis. Frothing or bubbling may be detectable in the top-down or oblique images if severe enough, and the system can alert the operator that a new sample may be needed. In some embodiments, anomalous qualities of a sample can also be detected. For example, a heterogenous image or object in a tube may indicate debris or sample contamination, if severe enough to appear in an image. Other qualities can also be observed. An estimation of fluid height can also be determined by image analysis of the top-down or oblique images, which may provide an early alert that additional fluid volume may be needed. In some embodiments, errors about the condition of trays can be determined via image analysis of the top-down or oblique images. For example, the presence of a spill in a slot of a tray may be determined if a sheen or other optical anomaly is observed. Similarly, the presence of debris or an object can be determined if the normal pattern consistent with a tube or empty slot is not observed, but anomalous content is. Furthermore, if marks or structures in a tray are outside of expected patterns (such as barcodes, or QR codes, or localization markers), this can indicate that the tray is worn or damaged. An operator can be alerted if any of these conditions exist.

These characteristics are obtained with no contact with the tubes 130, the tube tray 120, or the drawer 110. Instead, by obtaining images in different perspectives, stereoscopic analysis can be performed on the images. For example, the height of a tube 130 may be determined by comparing how much the center of a tube top shifts between subsequent images. In a similar manner, various other characteristics of the tubes 130 and the tube tray 120 may be determined.

Figure 3:
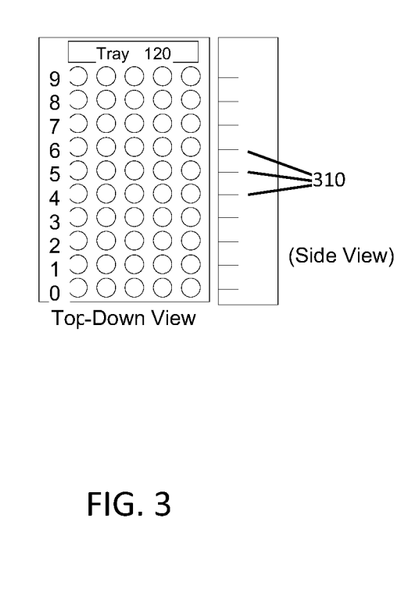
FIG. 3 shows an encoding representation used for characterizing tube trays and tubes held in a drawer through image analysis, according to an embodiment.

To determine when a row of the tube tray 120 is moved into a centered or substantially centered position beneath the one or more cameras, an encoding technique can be used, as illustrated in FIG. 3. The drawer 110 or the tube tray 120 can be encoded to determine the position of the drawer 110 or the tube tray 120 with respect to its orientation with the image capture system 140 and its placement within the work envelope 105. A notch 310, such as an optical notch or a magnetic notch, is encoded in the drawer 110/tube tray 120 for each row of the tube tray 120. According to an embodiment, a home position indicates when the drawer 110 is fully closed. When the drawer 110/tube tray 120 begins to move, an encoder is incremented. In an embodiment, a quadrature encoder is utilized to indicate in which direction the drawer 110/tube tray 120 is moving. With a quadrature encoder and a home position, the direction of movement as well as the absolute position is known because pulses are counted as the drawer 110/tube tray 120 is moved. As the drawer 110/tube tray 120 is pushed in, each time another row is centered under the cameras of the image capture system 140 (i.e., a notch 310 is encountered), the cameras are triggered to take an image.

In other embodiments, other encoding schemes may be implemented. For example, rather than encoding each row with a notch, such as the notch 310, every other row may be encoded, a center point between adjacent rows may be encoded, or the entire drawer 110 may be encoded and two positions may be determined through calibration or visual markings on the tray surface.

Figure 4:
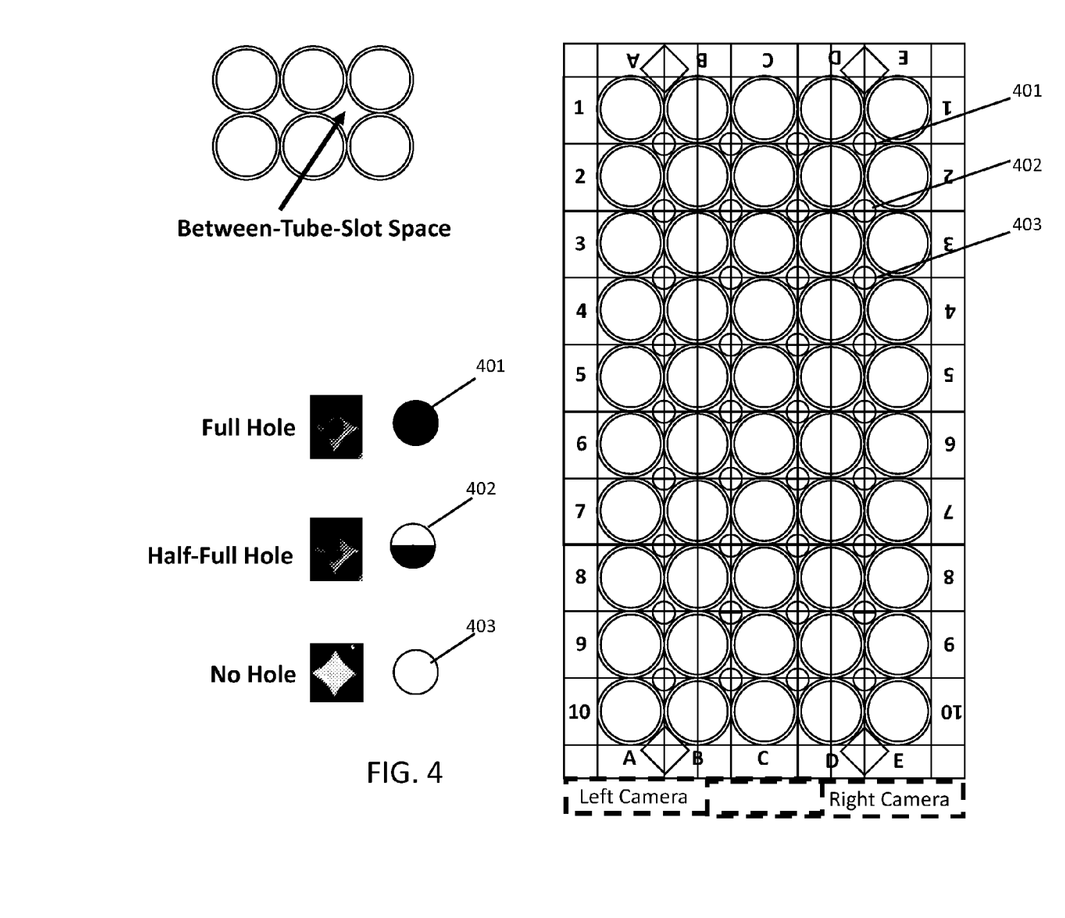
FIG. 4 shows an identification representation used for characterizing tube trays and tubes held in a drawer through image analysis, according to an embodiment.

FIG. 4 illustrates an identification representation used in the characterizing of the tube trays 120 and tubes 130, according to an embodiment. Visual markings 401, 402, and 403 are provided on the surface of the tray 120 to provide a verification of the row of the tubes 130 captured in the image in the event of offsetting when the images are taken. According to an embodiment, each image includes at least two between-tube-slot spaces, as illustrated in FIG. 4. In the example tray 120 provided in FIG. 4, there are ten rows with nine rows of spaces between the ten rows of tube slots. By using a three-value mold (i.e., a visual marking 401, 402, or 403) in each space, there are nine unique two-space combinations, one for each space row. Additionally, the half-full hole 402 indicates the tray orientation. Other representations and visual markings can be employed to aid in the identification of the row in the tube tray 120. For example, additional or fewer visual markings can be used depending on the number of rows and columns in the tube tray 120. The visual markings 401, 402, and 403 may be holes, indentations, or other markings that are molded into the surface of the tube tray 120. The visual markings are, according to an embodiment, dirt and wear-resistant.

The visual markings 401, 402, and 403 can also be used for localization within the tray coordinate system. The latency between the encoder-generated trigger and the actual image capture by the image capture system 140 means that the exact location of the tray 120 within the image is not known. The visual markings 401, 402, and 403 enable localization that overcomes the latency challenge and eliminates the need for precise calibration of the encoding system, the trays, and the image capture system 140.

Figure 5A:
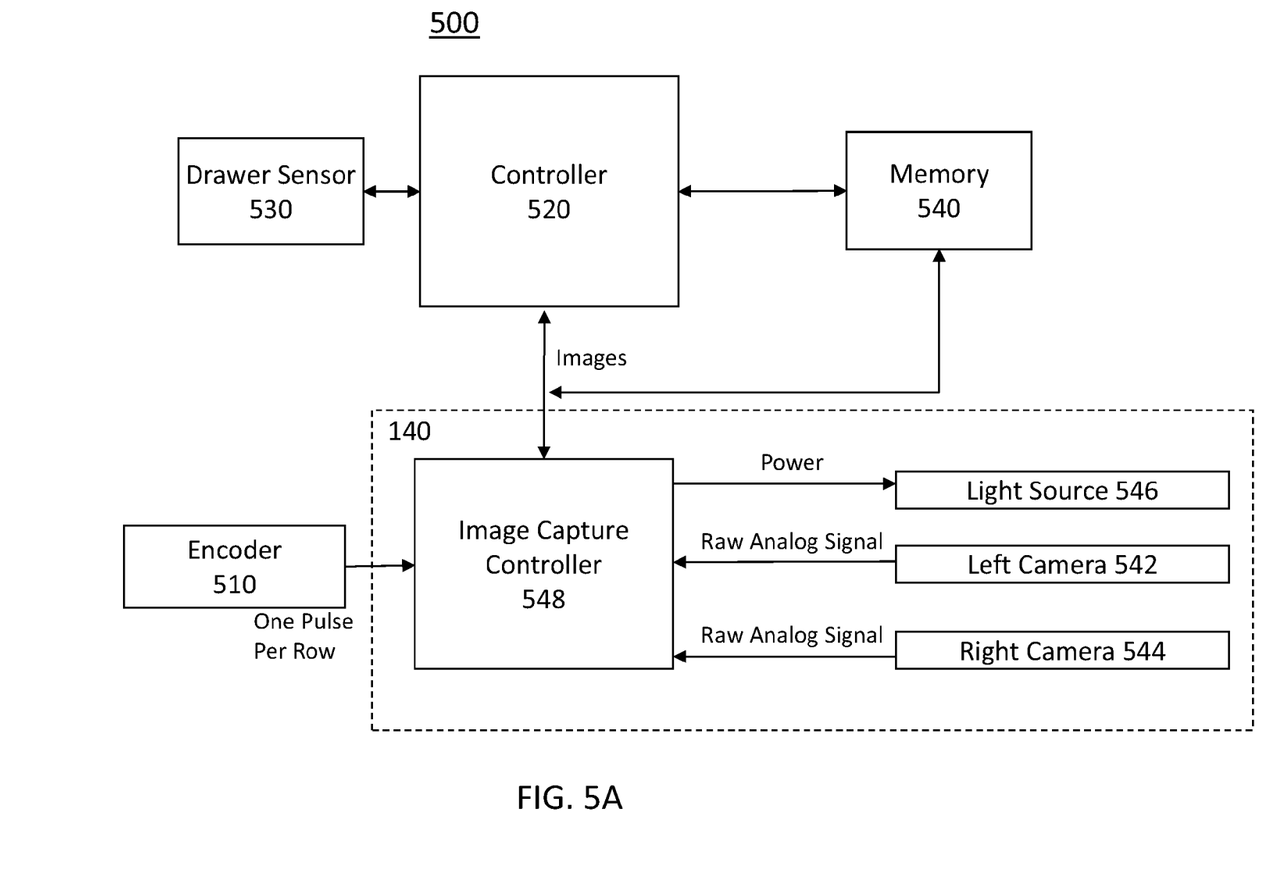
FIG. 5A illustrates a block diagram representation of a system for characterizing tube trays and tubes held in a drawer through image analysis, according to an embodiment.

FIG. 5A shows a block diagram representation of a system 500 for characterizing, through image analysis, the tube trays 120 and the tubes 130 contained thereon held in a drawer 110, according to an embodiment. The image capture system 140, according to an embodiment, includes two cameras, a left camera 542 and a right camera 544. Additional or fewer cameras may be included depending on the size of the drawers 110 and the tube trays 120, as well as the desired image quality and image perspective. A light source 546 and an image capture controller 548 are also part of the image capture system 140.

In an embodiment, in order to accurately capture the image and taking into account that the drawer 110/tube tray 120 is moving, the cameras 542, 544 use a shutter speed fast enough to essentially produce stop motion photography for capturing the images. In some embodiments, the light source 546 may be synchronized with the triggering of the cameras 542, 544 to aid in strobe or stop motion photography. In other embodiments, the light source 546 may be on continuously or may be triggered upon a first detection of movement of a drawer 110/tube tray 120. In some embodiments, cameras that are capable of a 250 microsecond exposure time are used. In other embodiments, cameras with other capabilities may be used depending on, for example, lighting, the speed of the drawer 110/tube tray 120, and the desired quality of the images.

With further reference to FIG. 5A, an encoder 510, such as a quadrature encoder, is used, as described above with reference to FIG. 3, to determine when a row of the tube tray 120 is moved into a centered or substantially centered position beneath the one or more cameras 542, 544. The encoder 510 transmits a signal (i.e., a pulse) to the image capture controller 548 upon detection of movement of the tube tray 120 corresponding to a new row of the tube tray 120 moving into a centered or substantially centered position beneath the one or more cameras 542, 544. The detection is based upon the encoder 510 incrementing upon a notch 310 being encountered, the notch 310 indicating that the drawer 110 and/or the tube tray 120 has been moved one row. The signal serves as an instruction for the image capture controller 548 to instruct the cameras 542, 544 to take an image upon receipt of the signal. As described above, in some embodiments, the encoding scheme may correspond to other movements, such as, for example, the drawer 110/tube tray 120 moving two rows or the drawer 110/tube tray 120 moving into a position centered between two rows. The image capture controller 548 manages the storage of the images taken by the cameras 542, 544 during a time period in which the drawer 110/tube tray 120 is being moved into the work envelope 105. This time period may also include the drawer 110/tube tray 120 being moved out of the work envelope 105 (e.g., the drawer 110/tube tray 120 may be pushed into the work envelope 105, partially pulled out of the work envelope 105, then pushed back into the work envelope 105). One or more internal or external memory buffer devices may be associated with the image capture controller 548, such as memory device 540. In one embodiment, one of the one or more memory devices comprises random access memory (RAM) in which a table is stored, the table containing the images taken by the cameras 542, 544. The image capture system 140 may capture additional rows of images at the beginning and end of each drawer 110/tube tray 120 in order to ensure that all rows in the tray are seen from the same number of perspectives (otherwise the rows at the end will not be captured from one side).

Additionally, the image capture system 140 may capture extra rows of images for all rows in order to generate additional perspectives on each tube and to aid in the determination of certain features. The image capture system 140 may also capture extra rows of images in order to detect features in the sample handler work envelope 105 in order to localize the trays 120 within the work envelope 105 and auto-calibrate the trays 120 to the sample handler's coordinate system. The image capture system 140 captures a fixed number of rows of images, at predetermined locations that have a fixed relationship to features of the trays 120 and sample handler work envelope 105.

The image capture system 140 may capture and store a single image corresponding to each image of a predetermined imaging position for the tray. For example, if a tray has 10 rows, and each row should appear in three adjacent images to provide two oblique perspectives and one substantially central perspective of each row, twelve images of the tray taken at twelve sequential imaging positions can be stored. When a new image of a particular perspective for a given row is captured, the previously stored image corresponding to that imagining position is overwritten. For example, consider the following scenario: an image is captured when row 10 is pushed into the drawer 110 and is centered or substantially centered beneath the cameras 542, 544 of the image capture system 140. If, subsequently, the drawer 110 is pulled out and then pushed in so that row 10 is again centered or substantially centered beneath the image capture system 140, a second image of this perspective is taken. This second image overwrites the first image. This implementation results in a fixed amount of storage as well as a fixed amount of processing time.

In some embodiments, images can be buffered until a drawer is fully closed. The buffering of images until the drawer 110 is fully closed and triggering the cameras 542, 544 on fixed positions can overcome challenges associated with random drawer movement. In particular, images are not acquired unless a fixed position of the drawer 110 is centered or substantially centered beneath the one or more cameras 542, 544, causing slight movements, such as an accidental bump, of the drawer 110 to be ignored by the image capture system 140. As a result, a set of images taken at predetermined imaging positions relative to the drawer 110 is available for subsequent processing to determine characteristics of tubes 130 and the drawer 110.

A controller 520 is provided for managing the image analysis of the images taken by the cameras 542, 544. Upon detection of the closing of the drawer 110, the image capture controller 548 provides the images to the controller 520 for downloading and processing. The controller 520 is, according to an embodiment, part of a sample handler that is used in the IVD environment to handle and move the tube trays 120 and the tubes 130 between storage locations, such as the work envelope 105, to analyzers. The image analysis performed by the controller 520 serves to instruct the sample handler on the various determined characteristics of the tube tray 120 and the tubes 130, thus allowing the sample handler to accordingly handle and process the tube tray 120 and the tubes 130.

The one or more memory devices 540 are associated with the controller 520. The one or more memory devices 540 may be internal or external to the controller 520.

One or more drawer sensors 530 may be connected to the controller 520 to indicate when the drawer 110 is fully closed and/or when the drawer 110 is fully opened. According to an embodiment, the drawer 110 being fully closed serves as an indication to begin image processing of the captured and stored images. When the drawer 110 is fully closed, the drawer sensor 530 sends a signal to the controller 520.

Figure 5B:
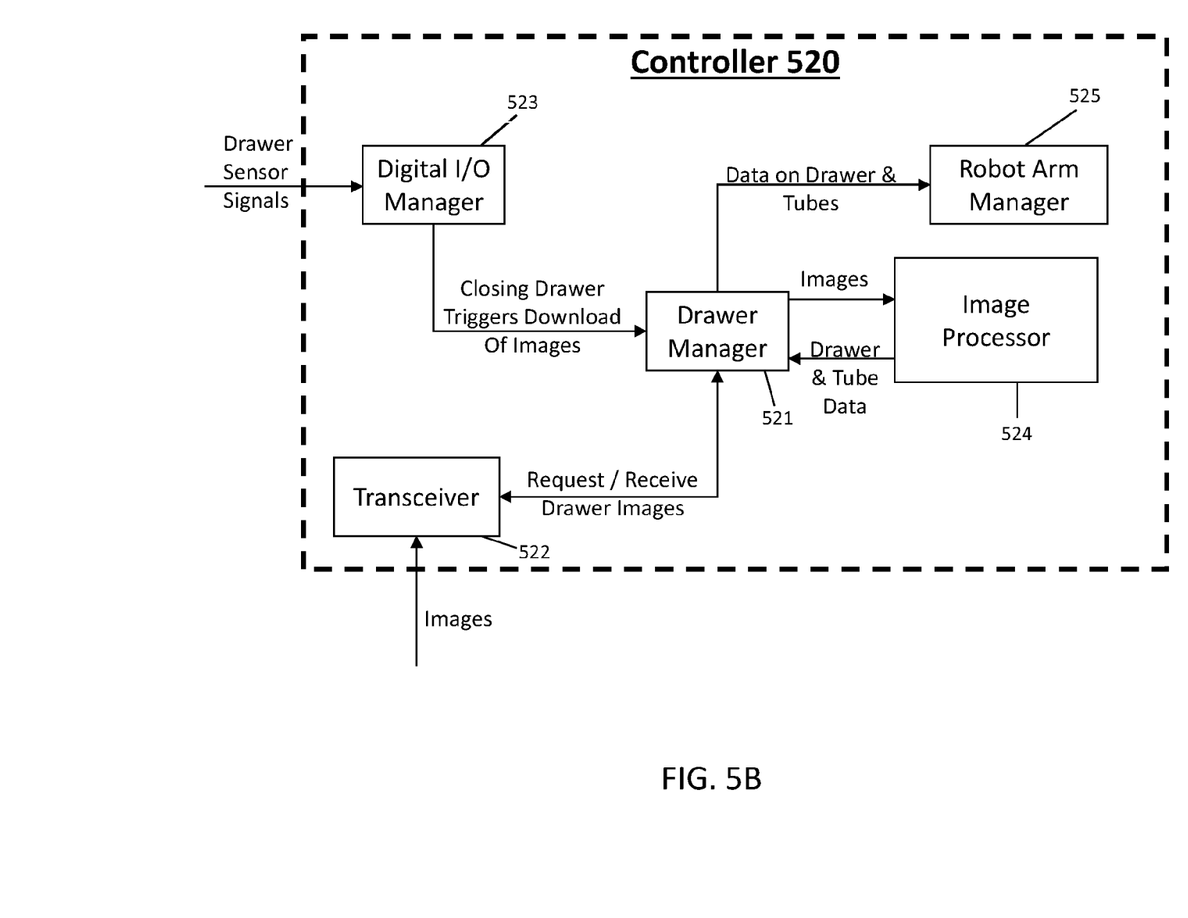
FIG. 5B shows a block diagram representation of a controller of the system shown in FIG. 5A.

FIG. 5B provides a block diagram representation of the controller 520, according to an embodiment. A drawer manager 521 manages the data flow amongst the various modules of the controller 520. A transceiver 522, which may, according to some embodiments, be a USB transceiver, receives data (i.e., the images captured) from the image capture controller 548. A digital input/output (I/O) manager 523 manages the receipt and transmission of signals between the drawer sensor 530 and the controller 520. When the I/O manager 523 receives a signal from the drawer sensor 530 indicating that the drawer 110 is fully closed, the I/O manager 523 conveys this signal to the drawer manager 521, which issues a request to the transceiver 522 to download the images. The drawer manager 521 provides the downloaded images to the image processor 524 for processing thereof. The data processed by the image processor 524, which includes the characteristics of the tube tray 120 and the tubes 130 thereon, may be sent to a robot arm manger 525 via the drawer manager 521. The robot arm manager 525 is the module of the controller 520 that is associated with handling and transport of the tube tray 120 and the tubes 130 (i.e., the sample handler). Thus, the robot arm manager 525 utilizes the data processed by the image processor 524.

The image processor 524 processes, according to an embodiment, the images based on a first-in/first-out algorithm. Thus, the robot arm manager 525 may be processing/handling the tubes 130 of the first row while the image processor 524 is processing the images related to the second row. Since the robot arm manager 525 does not require all of the characteristics data at the same time, the image processor 524 is not required to have all of the image data processed by the time the robot arm manager 525 is ready to begin its functions. According to an embodiment, the time required for the robot arm manager 525 to process a row of tubes 130 is approximately 30 seconds, thus allowing the image analysis performed by the image processor 524 to take up to 30 seconds per row. Thus, while the image capture is real-time, the image analysis is not real-time. This greatly reduces the required processing speed and capabilities of the image processor 524.

Figure 6:
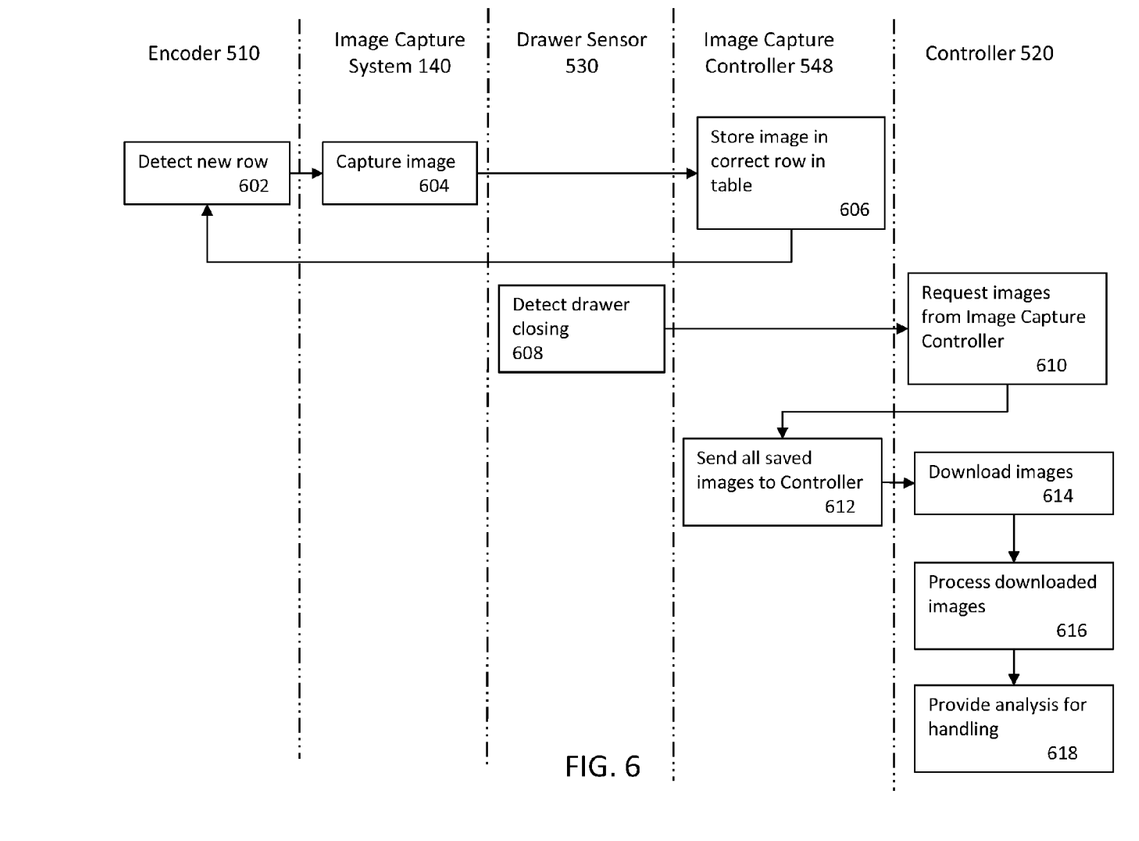
FIG. 6 is a data flow representation of the image capture and image analysis, resulting in the determination of the characteristics of the tube tray and the tubes, according to an embodiment.

FIG. 6 provides a data flow representation of the image capture and image analysis that results in the determination of the various characteristics of the tube tray 120 and the tubes 130.

At 602, the encoder 510 detects a new row has moved into focus of the one or more cameras 542, 544. At 604, the image capture system 140 captures the image based upon the signal received from the encoder 510. In some embodiments, images corresponding to a predetermined number of imaging positions can be stored in a table or array with the same number of rows as imaging positions (allowing multiple cameras to store corresponding images in corresponding columns in the array or table). At 606, the image capture controller 548 stores the image in a corresponding row in a table. This process is repeated each time a new row moving into focus is detected by the encoder.

When the drawer sensor 530 detects the closing of a drawer 110, at 608, a signal is sent to the controller 520. At 610, the controller 520 uses this signal to initiate downloading of the images stored in the image capture controller 548. At 612, the images are sent from the image capture controller 548 to the controller 520. At 614, the controller 520 downloads the images. At 616, the images are processed by the controller 520 to determine the characteristics of the tubes 130 and/or the tube tray 120. At 618, image analysis, which is the result of the processing of the images, is provided to assist in the handling of the tube tray 120 and the tubes 130. Upon determination of the tube characteristics, the image processor 524 may also store the determined characteristics in a database that is accessible to the sample handler, an automation system, and any analyzers attached to the automation system. As described above, the processing of the images is performed to obtain characteristics of the tube tray 120 and the tubes 130. By obtaining images in different perspectives, analysis can be performed on the images to determine, for example, the height and diameter of a tube 130. Other characteristics may be determined from one perspective, such as identifying a barcode on a top surface of a cap on a tube 130 or determining if a tube 130 contains a cap or tube-top cup.

The characteristics that may be determined by the image processor 524 include, but are not limited to, the following: a height of one or more tubes 130, a diameter of one or more tubes 130, a center point of one or more tubes 130, whether one or more tubes 130 have a cap or tube-top cup, a barcode on a top surface of a cap on one or more tubes 130, a color of a cap on one or more tubes 130, a type of a cap or tube-top cup on one or more tubes 130, an orientation (e.g., x-y-z location and/or tilt) of one or more tubes 130, and the tray slots containing a tube 130. The image processor 524 can also be used to perform any of the other analysis discussed throughout.

In another embodiment, the analysis of the images may be used to detect if a tube 130 has been added or removed since the tray 120 was last imaged. Upon detection of a newly added tube 130, special attributes may be assigned to the newly added tube 130. For example, in response to a STAT signal received by the controller 520 (e.g., a "STAT button" pressed before the drawer 110 is processed), a STAT attribute may be associated with the newly added tube 130.

Parameters and calibration information pertaining to the drawer 110, the tube tray 120, and the tubes 130 may need to be accessed to aid in the image analysis. Such parameter and calibration data may be stored in one or more look-up tables that are stored in memory (such as the memory device 540) accessible by the image processor 524. For example, referring to FIGS. 2C and 2F in the series of two images for row 10, one tube 130 is in the center of the image while two tubes 130 are slightly off-center. In determining certain characteristics of the off-center tubes 130, a calibration may need to be applied to take into account the off-centeredness of one or more tubes 130. Such calibration data is stored in one of the look-up tables, according to an embodiment. A characterization of tube type properties is another example of the data that may be stored in the look-up tables. According to an embodiment, there are a fixed number of types of tubes that are contained and handled in the work envelope 105. Storing data related to the properties of each type of tube may be beneficial in determining the characteristics related to a particular tube 130; for example, if a measurement performed by the image processor 524 is inaccurate, referring to the data related to the tube properties may assist in confirming characteristics related to the tube 130, allowing the nearest matching known tube type to be determined and those known characteristics to be substituted for the observed characteristics of the tube in the images.

In addition to the characteristics of the tubes 130, information related to the drawer 110 may also be determined. For example, the encoder 510 may be used to determine if the drawer 110 is being closed at an unsafe speed. The controller 520 may determine the frequency of images being taken, thus determining the speed at which the drawer 110 is being moved. If the speed exceeds a predetermined acceptable value, a signal may be generated to warn an operator.

Moreover, the characteristics determined by the image processor 524 may be used with other data for enhanced feature detection. For example, the determined characteristics may be combined with side perspective images to identify further characteristics of the tubes 130.

Some embodiments of the systems and methods described herein can also be used outside of a laboratory environment. For example, the embodiments have been described in the context of fluid samples in tubes in an IVD lab. However, this is merely intended as illustrative. The same principles could be extended to other environments where objects are organized on containers or shelves, for example. For example, the systems and methods described herein can be used in a shipping or manufacturing environment where, instead of samples, the items being analyzed are items being shipped (e.g., goods or packages intended for a destination) or component parts of a custom product (e.g., instead of sample tubes, the objects being analyzed could be individual components that are custom made or otherwise intended for a given customer's product).

For example, the sample tube/containers described herein could be replaced with any objects, such as boxes or widgets. Accordingly, the sample tubes/containers in the embodiments described herein can be considered illustrative. It will be appreciated that some embodiments analyze other objects, and any suitable items may be substituted for the sample tubes into the illustrative embodiments. The parts for a customer's products could be stored in ordered trays (which could be large bins, containers, or palettes). Trays can be considered a type of container, and each embodiment disclosed throughout can be considered to also contemplate the use of containers generally. Some embodiments of trays may also include one or more shelves.

The controllers 520 and 548 may be a processing device, computing device, or the like for performing calculations and operations described herein. As used herein, a controller or a processor should be understood to include any number of controllers or processors. While the controllers and processors described herein have been broken down as individual controllers and processors performing certain tasks, this is done for illustrative purposes. Embodiments of the present invention can include single or multiple controllers or processors performing the roles described. Furthermore, the roles described as separate controllers or processors herein can, in some embodiments, be performed by separate or common controllers or processors or any subset therein.

The controllers 520 and 548 interface with one or more of the encoder 510, the drawer sensor 530, the cameras 542, 544, and the light source 546, and may also interface with one or more memory devices, including memory device 540, and other memory devices such as read only memory (ROM), random access memory (RAM), and one or more optional non-transitory memory devices such as, for example, an external or internal DVD drive, a CD ROM drive, a hard drive, flash memory, a USB drive, or the like. The memory device 540 may be configured to include individual files and/or one or more databases for storing any software modules, instructions, or data.

Program instructions, software, or interactive modules for performing any of the functional steps associated with the processes as described above may be stored in the ROM and/or the RAM. Optionally, the program instructions may be stored on a tangible computer readable medium such as a compact disc, a digital disk, flash memory, a memory card, a USB drive, an optical disc storage medium, such as a Blu-Ray™ disc, and/or other recording medium.

An optional display interface may permit information from the controllers 520 and 548 to be displayed on a display in audio, visual, graphic, and/or alphanumeric format. Communication with external devices may occur using various communication ports that may be attached to one or more communications networks, such as the Internet or a local area network, or directly to a portable computing device such as a notebook computer. An interface may allow for receipt of data from input devices such as a keyboard, a mouse, a joystick, a touch screen, a remote control, a pointing device, a video input device, an audio input device, and the like.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A system for characterizing a tube tray handled by a sample handler in an in vitro diagnostics (IVD) environment, the tube tray configured to fit within a portion of a drawer that is movable between an open and a closed position and that is accessible by the sample handler, the tube tray comprising an array of rows and columns of slots, rows being oriented parallel to a face of the drawer and each slot being configured to hold a tube, the system comprising:
an image capture system comprising at least one overhead camera and a memory buffer, the image capture system configured to capture overhead images of the tube tray positioned in the drawer as the drawer is closed and temporarily store the captured images in the memory buffer for later analysis;
a position encoder in communication with the image capture system, the encoder configured to trigger the image capture system when each row of the tube tray in the drawer is at a predetermined position beneath the image capture system as the drawer is closed; and
one or more processors together configured to receive the captured images from the memory buffer after the drawer is closed and analyze the images,
wherein each camera of the image capture system captures a series of images that includes an image of each row captured responsive to the encoder as each row passes below the camera, each image of a row having an overhead view of tubes in that row and oblique views of tubes in adjacent rows, such that each tube appears in images of adjacent rows; and
wherein the one or more processors process the series of images to determine physical characteristics related to each tube in the tray by analyzing the overhead and oblique views of each tube in successive images.

2. The system of claim 1, wherein the images of adjacent rows within the series of images provide different perspectives of tubes in a first row and the one or more processors analyze the images of adjacent rows to determine a height of each tube.

3. The system of claim 1, further comprising a drawer sensor configured to detect one or more of (i) the drawer being fully closed and (ii) the drawer being fully opened; wherein the drawer sensor signals to the one or more processors upon detection of the drawer being fully closed.

4. The system of claim 3, wherein the one or more processors begin the processing of the series of images upon receipt of the signal from the drawer sensor.

5. The system of claim 1, wherein the image capture system is further comprised of a lighting source.

6. The system of claim 1, wherein the physical characteristics related to the tubes are communicated to a module of the sample handler.

7. The system of claim 1, wherein the physical characteristics related to the tubes comprise a height of each tube, a diameter of each tube, and one or more of: a center point of one or more tubes, whether one or more tubes have a cap or tube-top cup, barcode information on a top surface of a cap on one or more tubes, a color of a cap on one or more tubes, a type of a cap or tube-top cup on one or more tubes, a type of tube, a type of sample, a priority of the tubes, an orientation of one or more tubes, and the tube tray slots containing a tube.

8. The system of claim 1, wherein the physical characteristics related to the tubes comprise one or more of: detecting the presence of condensation on at least one tube, detecting the presence of bubbles in at least one tube, detecting a fluid height of a fluid in at least one tube, detecting damage to at least one tube, detecting one or more anomalous quality of a sample contained in at least one tube, and detecting problems with a barcode on at least one tube.

9. The system of claim 1, wherein the one or more processors process the series of images to determine one or more characteristics of the tube tray, comprising at least one of: an identity of the tube tray, the presence of debris or spillage in a slot of the tube tray, an orientation of the tube tray, and damage to the tube tray.

10. The system of claim 1, wherein the tube tray comprises visual markings on the tray between slots to identify the rows of the tube tray, wherein the one or more processors use the visual markings to confirm an identity of the row in the series of images being processed.

11. The system of claim 1, further comprising one or more memory devices, the one or more memory devices comprising look-up tables containing parameter and calibration data related to the tubes, the look-up tables accessible by the one or more processors when processing the series of images.

12. A method of characterizing tube trays handled by a sample handler in an in vitro diagnostics (IVD) environment, each tube tray configured to fit within a portion of a drawer that is movable between an open and a closed position and that is accessible by the sample handler, the tube tray comprising an array of rows and columns of slots, rows being parallel to a face of the drawer and each slot configured to hold a tube, the method comprising:

detecting, by a position encoder when each row of the tube tray in the drawer is at a predetermined position beneath the image capture system;

capturing, by an image capture system comprising at least one overhead camera, a series of images of the tube tray positioned in the drawer, the series including an image of each row captured responsive to the encoder as each row passes below the at least one overhead camera as the drawer is closed, each image of a row having an overhead view of tubes in that row and oblique views of tubes in adjacent rows, such that each tube appears in images of adjacent rows;

storing, temporarily as the drawer is closed, the series of images in a memory buffer for later analysis;

receiving, by one or more processors in communication with the image capture system, the captured images from the memory buffer after the drawer is closed; and analyzing, by the one or more processors, the images to determine physical characteristics related to each tube in the tray by analyzing the overhead and oblique views of each tube in successive images.

13. The method of claim 12, wherein the images of adjacent rows within the series of images provide a different perspectives of tubes in a first row and the one or more processors analyze the images of adjacent rows to determine a height of each tube.

14. The method of claim 12, further comprising:

detecting, by a drawer sensor, one or more of (i) the drawer being fully closed and (ii) the drawer being fully opened, wherein the drawer sensor signals to the one or more processors upon detection of the drawer being fully closed.

15. The method of claim 14, wherein the one or more processors begin the processing of the series of images upon receipt of the signal from the drawer sensor.

16. The method of claim 12, wherein the image capture system is further comprised of a lighting source.

17. The method of claim 12, wherein the physical characteristics related to the tubes are communicated to a module of the sample handler.

18. The method of claim 12, wherein the physical characteristics related to the tubes comprise a height of each tube, a diameter of each tube, and one or more of: a center point of one or more tubes, whether one or more tubes have a cap or tube-top cup, barcode information on a top surface of a cap on one or more tubes, a color of a cap on one or more tubes, a type of a cap or tube-top cup on one or more tubes, a type of tube, a type of sample, a priority of the tubes, an orientation of one or more tubes, and the tube tray slots containing a tube.

19. The method of claim 12, wherein the physical characteristics related to the tubes comprise one or more of: detecting the presence of condensation on at least one tube, detecting the presence of bubbles in at least one tube, detecting a fluid height of a fluid in at least one tube, detecting damage to at least one tube, detecting one or more anomalous quality of a sample contained in at least one tube, and detecting problems with a barcode on at least one tube.

20. The method of claim 12, wherein the one or more processors process the series of images to determine one or more characteristics of the tube tray, comprising at least one of: an identity of the tube tray, the presence of debris or spillage in a slot of the tube tray, an orientation of the tube tray, and damage to the tube tray.

21. The method of claim 12, wherein the step of analyzing further comprises identifying visual markings on the tube tray between slots to identify the rows of the tube tray, wherein the one or more processors use the visual markings to confirm an identity of the row in the series of images being processed.

22. The method of claim 12, wherein the one or more processors utilize look-up tables containing parameter and calibration data related to the tubes.

* * * * *